US005573008A

United States Patent [19]

Robinson et al.

[11] Patent Number: 5,573,008
[45] Date of Patent: Nov. 12, 1996

[54] MULTIPLE BIOPSY SAMPLING CORING DEVICE

[75] Inventors: Donald E. Robinson, Hopkinton, Mass.; Michael S. Banik, Cincinnati, Ohio

[73] Assignee: Boston Scientific Corporation, Natick, Mass.

[21] Appl. No.: 146,447

[22] Filed: Oct. 29, 1993

[51] Int. Cl.[6] .................................................. A61B 10/00
[52] U.S. Cl. ................................................................ 128/754
[58] Field of Search .................................. 128/751–754; 606/167, 170

[56] References Cited

U.S. PATENT DOCUMENTS

| | | |
|---|---|---|
| 612,569 | 10/1898 | Moscrop . |
| 668,647 | 2/1901 | Jaenicke . |
| 1,162,901 | 12/1915 | Cantey . |
| 1,606,497 | 11/1926 | Berger . |
| 1,867,624 | 7/1932 | Hoffman . |
| 1,891,054 | 12/1932 | Pitman . |
| 2,426,535 | 8/1947 | Turkel . |
| 2,493,979 | 1/1950 | Kudd . |
| 2,541,542 | 2/1951 | Perez et al. . |
| 2,749,909 | 6/1956 | Ullery et al. ................................. 128/2 |
| 3,001,522 | 9/1961 | Silverman . |
| 3,175,554 | 3/1965 | Stewart . |
| 3,181,533 | 5/1965 | Heath . |
| 3,342,175 | 9/1967 | Bulloch . |
| 3,477,423 | 11/1969 | Griffith ........................................ 128/2 |
| 3,683,892 | 8/1972 | Harris ........................................... 128/2 |
| 3,692,020 | 9/1972 | Schied .......................................... 128/2 |
| 3,732,858 | 5/1973 | Banko .......................................... 128/2 |
| 3,882,849 | 5/1975 | Jamshidi ...................................... 128/2 |
| 3,902,498 | 9/1975 | Niederer .................................... 128/305 |
| 3,903,892 | 9/1975 | Komiya ..................................... 128/303 |
| 3,955,578 | 5/1976 | Chamness et al. ........................ 128/303 |
| 3,989,033 | 11/1976 | Halpern et al. ............................. 128/2 |
| 5,211,655 | 5/1993 | Hasson ...................................... 606/205 |
| 5,224,488 | 7/1993 | Neuffer ..................................... 128/751 |
| 5,238,002 | 8/1993 | Devlin et al. ............................. 128/751 |
| 5,242,461 | 9/1993 | Kortenbach et al. ..................... 606/159 |
| 5,251,641 | 10/1993 | Xavier ...................................... 128/754 |
| 5,267,572 | 12/1993 | Bucalo ...................................... 128/754 |
| 5,373,854 | 12/1994 | Kolozsi ..................................... 128/749 |
| 5,375,608 | 12/1994 | Tiefenbrun et al. ...................... 128/754 |
| 3,989,049 | 11/1976 | Yoon ......................................... 128/326 |
| 3,996,935 | 12/1976 | Banko ....................................... 128/276 |
| 4,007,732 | 2/1977 | Kvavle et al. . |
| 4,020,847 | 5/1977 | Clark, III . |
| 4,168,698 | 9/1979 | Ostergard .................................. 128/751 |
| 4,174,715 | 11/1979 | Hasson ..................................... 128/321 |
| 4,178,810 | 12/1979 | Takahashi ................................... 74/501 |
| 4,200,111 | 4/1980 | Harris ....................................... 128/751 |
| 4,220,155 | 9/1980 | Kimberling et al. .................... 128/306 |
| 4,243,048 | 1/1981 | Griffin ...................................... 128/751 |

(List continued on next page.)

FOREIGN PATENT DOCUMENTS

| | | |
|---|---|---|
| 1215439 | 12/1970 | United Kingdom . |
| WO93/04630 | 3/1993 | WIPO . |

OTHER PUBLICATIONS

Radial Jaw Single–Use Biopsy Forceps, Boston Scientific Corporation, 1993.

Grossman, "Gastrointestinal Endoscopy", Clinical Symposia, vol. 32, No. 3, 1980.

*Primary Examiner*—Max Hindenburg
*Attorney, Agent, or Firm*—Fish & Richardson, P.C.

[57] ABSTRACT

A device and method for collecting from a tissue surface, a sample of tissue, including tissue specimens, polyps, or the like. A device body defines a forward-facing tissue receiving opening of substantially predetermined width through which tissue may pass when the opening is near the tissue surface. A severing element is actuatable across the width of the tissue receiving opening when tissue from the surface extends through the opening for severing the tissue from the surface. A storage space proximal of and adjacent the opening is provided for storage of multiple, successively taken samples by repeatedly passing tissue through the opening and actuating the severing element.

5 Claims, 13 Drawing Sheets

U.S. PATENT DOCUMENTS

| | | | |
|---|---|---|---|
| 4,282,884 | 8/1981 | Boebel | 128/751 |
| 4,326,530 | 4/1982 | Fleury, Jr. | 128/303 |
| 4,427,014 | 1/1984 | Bel et al. | 128/751 |
| 4,461,305 | 7/1984 | Cibley | 128/754 |
| 4,493,320 | 1/1985 | Treat | 128/303 |
| 4,522,206 | 6/1985 | Whipple et al. | 128/312 |
| 4,574,803 | 3/1986 | Storz | 128/305 |
| 4,620,547 | 11/1986 | Boebel | 128/754 |
| 4,631,052 | 12/1986 | Kensey | 604/22 |
| 4,651,752 | 3/1987 | Fuerst | 128/754 |
| 4,651,753 | 3/1987 | Lifton | 128/751 |
| 4,662,371 | 5/1987 | Whipple et al. | 128/312 |
| 4,682,606 | 7/1987 | DeCaprio | 128/754 |
| 4,693,257 | 9/1987 | Markham | 128/752 |
| 4,708,147 | 11/1987 | Haaga | 128/753 |
| 4,712,550 | 12/1987 | Sinnett | 128/334 R |
| 4,735,215 | 4/1988 | Goto et al. | 128/754 |
| 4,763,668 | 8/1988 | Macek et al. | 128/751 |
| 4,785,826 | 11/1988 | Ward | 128/754 |
| 4,830,002 | 5/1989 | Semm | 128/321 |
| 4,867,156 | 9/1989 | Stack et al. | 128/305 |
| 4,881,550 | 11/1989 | Kothe | 128/752 |
| 4,887,612 | 12/1989 | Esser et al. | 128/751 |
| 4,903,709 | 2/1990 | Skimmer | 128/754 |
| 4,926,877 | 5/1990 | Bookwalter | 128/754 |
| 4,936,845 | 6/1990 | Stevens | 606/159 |
| 4,971,067 | 11/1990 | Bolduc et al. | 128/751 |
| 4,976,269 | 12/1990 | Mehl | 128/754 |
| 4,986,825 | 1/1991 | Bays et al. | 604/22 |
| 5,026,379 | 6/1991 | Yoon | 606/141 |
| 5,052,402 | 10/1991 | Bencini et al. | 128/751 |
| 5,074,311 | 12/1991 | Hasson | 128/754 |
| 5,085,659 | 2/1992 | Rydell | 606/47 |
| 5,098,440 | 3/1992 | Hillstead | 606/108 |
| 5,111,828 | 5/1992 | Kornberg et al. | 128/754 |
| 5,133,360 | 7/1992 | Spears | 128/754 |
| 5,133,727 | 7/1992 | Bales et al. | 606/170 |
| 5,147,378 | 9/1992 | Markham | 606/206 |
| 5,148,813 | 9/1992 | Bucalo | 128/754 |
| 5,171,255 | 12/1992 | Rydell | 606/170 |
| 5,172,700 | 12/1992 | Bencini et al. | 128/751 |
| 5,195,533 | 3/1993 | Chin et al. | 128/754 |
| 5,197,484 | 3/1993 | Kornberg et al. | 128/754 |

MULTIPLE BIOPSY SAMPLING CORING DEVICE

FIELD OF THE INVENTION

This invention relates to taking samples of tissue from the body for biopsy analysis.

BACKGROUND OF THE INVENTION

Tissue samples can be examined in a laboratory to determine the presence of a pathological disorder (e.g. malignancy). Often, the samples must be obtained from deep within the body using a medical sampling instrument. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In a first aspect, the invention features a device for collecting from a tissue surface, a sample of tissue, including tissue specimens, polyps, or the like. The device includes a device body defining a forward-facing tissue receiving opening of substantially predetermined width through which tissue may pass when the opening is near the tissue surface. A severing element is actuatable across the tissue receiving opening when tissue from the surface extends through the opening for severing the tissue from the surface. A storage space proximal of and adjacent the opening is provided for storage of multiple, successively taken samples by repeatedly passing tissue through the opening and actuating the severing element.

Embodiments may include one or more of the following features. The severing element is a set of moveable jaw-like cutting members actuatable to be opened and closed for severing tissue from the surface to take the sample. The cutting members are coaxially disposed and axially positionable with respect to the tissue receiving opening such that the device is positionable between a first configuration in which the cutting-members are proximal of the opening and open for receiving tissue through the opening and a second configuration in which the cutting members are near the opening where the cutting members can be closed to sever tissue and take the sample. The cutting members are disposed over the device body. The cutting members are biased toward the closed configuration. The cutting members are opened by positioning the device in the first configuration, where the cutting members bear on outer surfaces of the body which oppose the bias force. The cutting members are closed by positioning the device in the second configuration where the cutting members are free from the body and close in response to the bias force. The forward-facing tissue-receiving opening is defined about its periphery by a tissue-cutting edge, where the tissue passes through the opening by urging the edge distally into the tissue surface. The device includes an axially movable retractor for engaging tissue and drawing it proximally. The retractor is extendable distally beyond the opening for engaging the tissue surface and retractable proximally to draw tissue through the tissue-receiving opening. The retractor is a spear-form element adapted to pierce tissue and has a retaining barb on its distal end. The severing element is a cutting loop, the cutting loop is actuatable between an open configuration that is oriented generally coaxially with the body defining the tissue-receiving opening and a closed configuration in which the loop passes across the opening to sever the tissue. The cutting loop is actuated by a control wire extending parallel with the axis of the body. The control wire passes through a lumen extending to an opening adjacent the tissue-receiving opening. The cutting loop is actuated by withdrawing it into the lumen. The retractor is extendable distally beyond the opening and the cutting loop for engaging the tissue surface and retractable proximally to draw tissue through the tissue-receiving opening and cutting loop. The retractor is a spear-form element adapted to pierce tissue and has a retaining barb on its distal end. The device includes a cutting guide on the outer surface of the body of the device proximal of the tissue-receiving opening. The guide is formed by a slot including a cutting edge with a portion communicating with the periphery of the opening such that tissue prolapses into the slot when the periphery of the device is placed against the tissue surface. The device is rotatable about its axis so that tissue in the slot is cut by the cutting edge and tissue passes through the tissue-receiving opening. The depth of the cut and the width of tissue passing through the opening is determined by the degree of rotation of the body and the width of the guide. The depth of the cut is about 1–2 mm for each rotation of the device. The severing element is a cutting edge positioned to extend radially across the opening. The element is actuatable to sever tissue by rotation of the wire across the opening of the device body. The cutting edge is a cutting wire extending across the diameter of the opening. The wire is attached under tension at its opposite ends to the body of the device. The wire is actuatable to sever tissue by rotation of the device about its axis. The storage portion includes apertures through the wall of the device. The storage portion includes a low friction coating to improve axial sliding of tissue samples.

In another aspect, the invention features a method for collecting from a sample surface, a sample of tissue, including specimens, polyps, or the like. The method includes providing a sampling device that has a device body defining a forward-facing tissue receiving opening of substantially predetermined width through which tissue may pass when the opening is near the tissue surface, and a severing element actuatable across the width of the tissue receiving opening when tissue from the surface extends through the opening for severing the tissue from the surface. The method includes positioning the device near the tissue surface, receiving tissue through the tissue-receiving opening, and actuating the severing element to sever a tissue sample from the surface.

Embodiments may include one or more of the following. The method includes providing the sampling device at the end of an elongate flexible member, and delivering the device by threading the device through the body to a desired tissue surface deep within the body. The method includes providing a sampling device that further includes a storage space proximal of and adjacent the opening for storage of multiple successively taken samples by repeatedly passing tissue through the opening and actuating the severing element, and taking multiple samples by repeating the steps of positioning and actuating to take multiple samples without removing the device from the body. The method includes rotating the device as it is urged forward into tissue.

The invention has many advantages. For example, sampling into tissue to a desired depth can be achieved by controlling the amount of sample that enters the forward-facing coring opening of the device, by, for example, controlling how deeply the device is advanced into a tissue wall or how much tissue is drawn through the opening using a retractor. Thick samples can be taken in a single sampling action; for example, samples beyond the mucosal layer (submucosal sampling) can be taken from a site in a single sampling action. Careful control of sampling depth also permits samples to be taken from very thin tissue walls without puncturing the walls. Multiple samples can be taken, stored in the device, and maintained in a hydrated state without removing the device from the body.

Further advantages follow.

BRIEF DESCRIPTION OF THE DRAWING

We first briefly describe the drawings.

DESCRIPTION OF THE PREFERRED EMBODIMENTS

Figure 1:
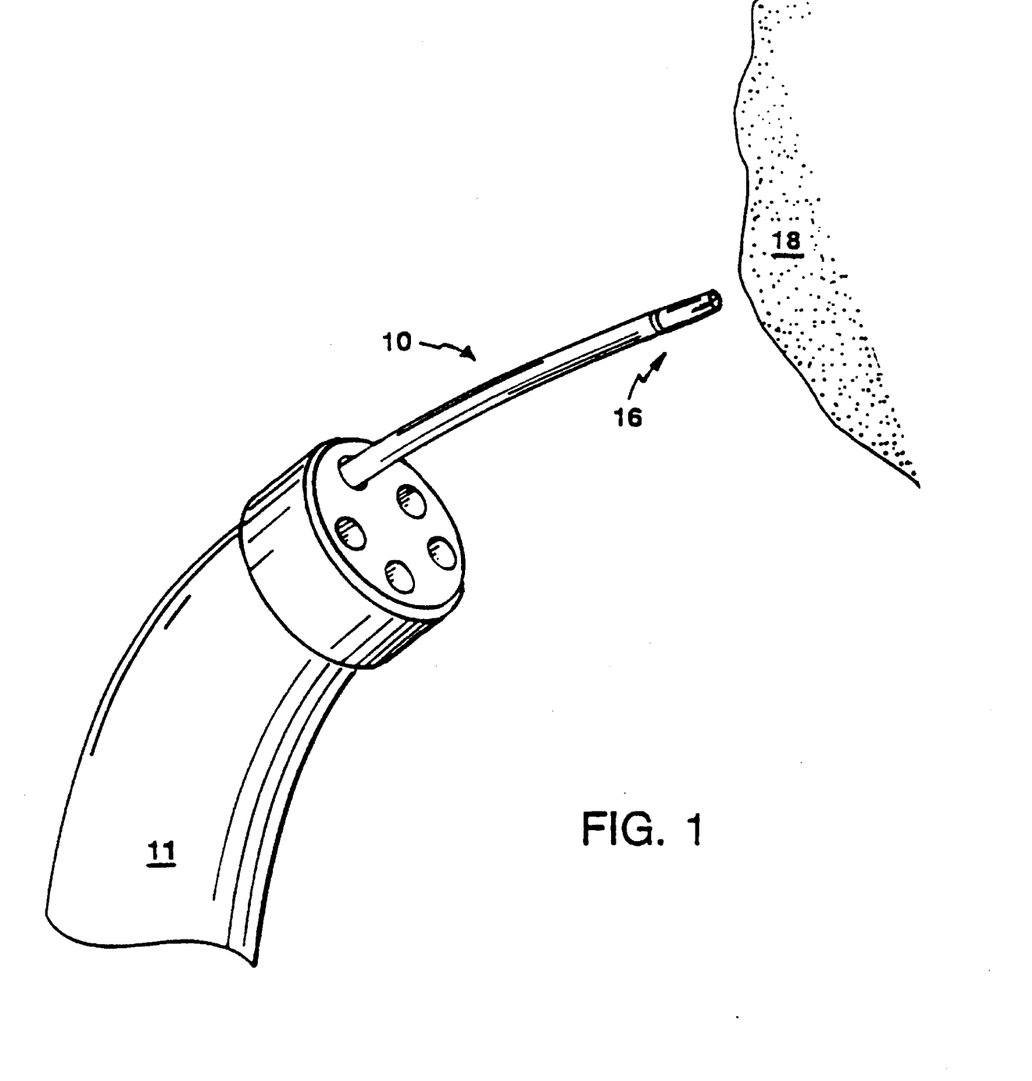
FIG. 1 is a perspective view of an embodiment of the invention being delivered into the body through an endoscope.
Figure 2:
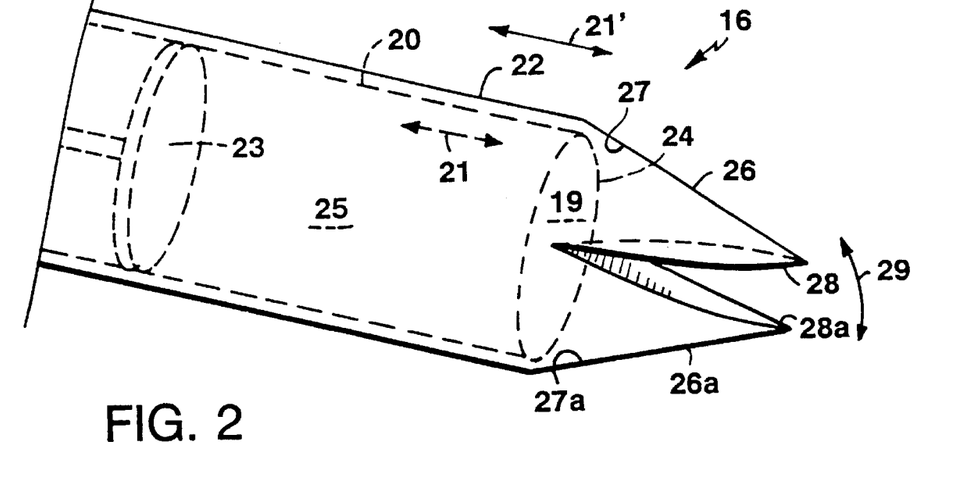
FIGS. 2–2e illustrate the structure and use of an embodiment of the invention.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g. from a surface in the gastrointestinal tract or bronchial tract). The device has a diameter of preferably around 1.8–2.4 mm, typically about 2.3 mm or less and is of sufficient flexibility so it passes easily though the channel when the endoscope follows a tortuous body passageway. The endoscope includes other lumens for water, air, suction, and viewing. Devices according to the invention can be adapted to be introduced to sites (e.g., urinary tract, reproductive organs, cardiac tissue, or the like) deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications, in breast biopsy in which the device is pressed directly into tissue, laproscopic biopsy in which the cutting element is positioned through a tubular instrument extending through the skin, and percutaneous needle biopsy in which the device is directed through a hole in the skin to sample an internal organ, e.g., the liver Referring to FIGS. 2–2e, in an embodiment, sampling portion 16 includes an inner tubular sample holding and coring member 20 and an outer cutting member 22. The inner tubular member 20 defines in its proximal portions an inner space 25 for storage of multiple, successively taken biopsy samples. As shown particularly in FIGS. 2a et seq., the samples are stored adjacent one another in the order in which they are taken. A sample stop 23 defines the most proximal end of the space 25. The stop 23 can be moved axially distally to retrieve the multiple samples after the device is removed from the body, as will be discussed in more detail below. The distal end of the inner tubular member defines a forward-facing, tissue-receiving opening 19 and is sharpened to a cutting edge 24.

The outer cutting member 22 includes near its distal end a pair of moveable jaw-like cutting elements 26, 26a. The cutting elements are formed of a material having substantial elasticity, for example, a shape memory alloy or stainless steel, and worked such that the cutting elements are biased toward the closed position. The cutting member 22 and the inner tubular member 20 are axially movable with respect to one another (arrows 21, 21'). In the configuration shown in FIG. 2, with the inner tubular member extended distally somewhat with respect to the cutting member 22, the distal end of the cutting member bears on the inner surfaces 27, 27a of the elements 26, 26a, moving them radially into an open position (arrow 29). The outer edges 28, 28a of the cutting elements are sharpened for cutting tissue, as will be further described below.

In embodiments, other cutting element arrangements are possible; for example, elements that rotate about a pivot point and are biased by a spring could be provided. Arrangements with more than two cutting elements may also be used. One of either the cutting member or tubular member may be moveable and the other stationary. The components that experience sliding motion may include a lubricant. For example, the interior wall of the inner tubular member may include a low friction coating 17, e.g., of teflon, silicone, or a hydrogel, so that samples within the tube and storage space slide easily. The outer surface of the inner tubular member and/or the inner surface of the outer tubular member may also include a lubricant to ease sliding motion. (Other sliding components in other embodiments, shown below, e.g., control wires and cutting loops may also include a lubricant.)

Figure 2A:
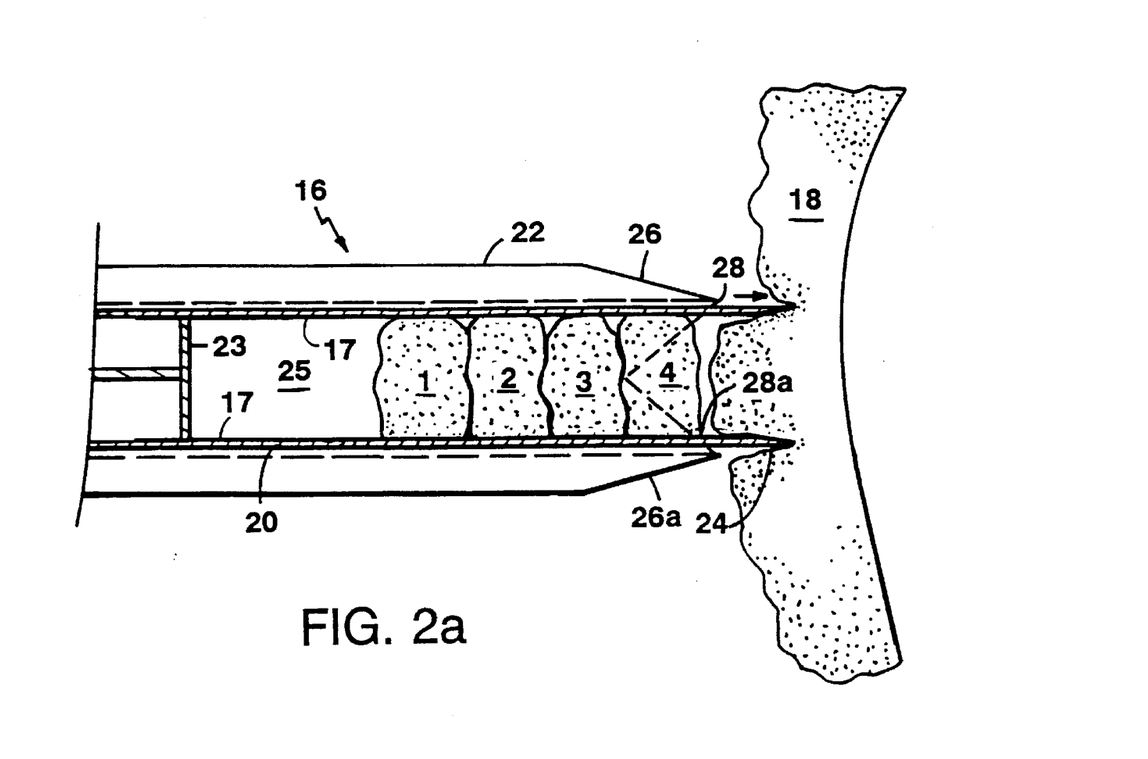

Referring particularly to FIG. 2a, (cross-sectional view), in use, the inner tubular member is extended distally to open the cutting elements and extend beyond them so the edge 24 cuts into a surface 18 of tissue to a depth that approximates the desired depth to which a sample is to be taken. The tubular member is rotated slightly about its axis as it is urged forward to create a shearing action that aids cutting.

Figure 2B:
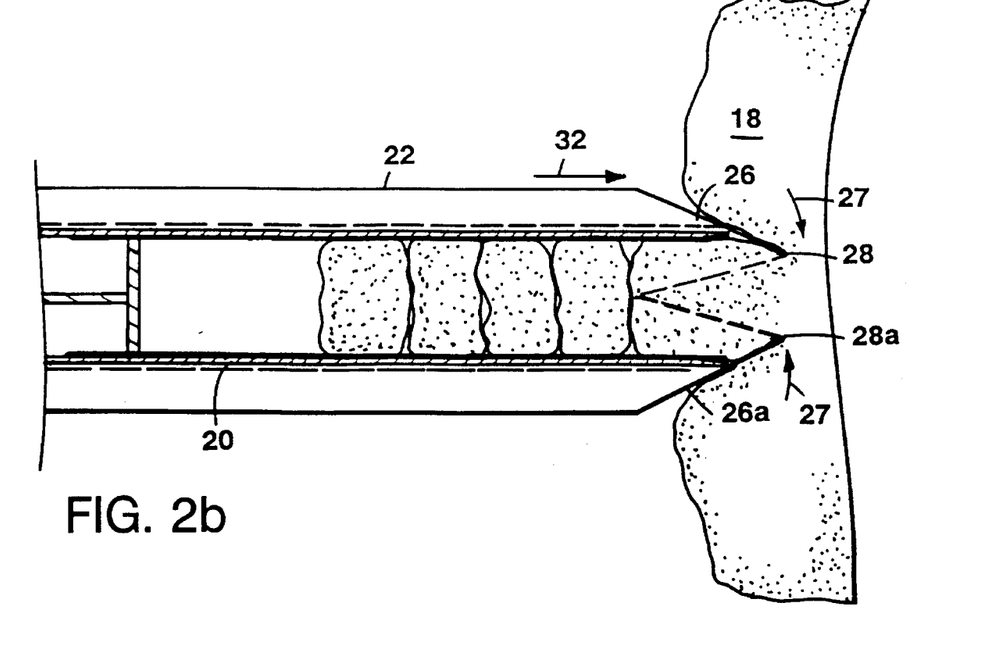

Referring particularly to FIG. 2b, the sample is severed from the tissue surface 18 by extending the outer cutting member 22 distally (arrow 32). When the cutting member 22 has extended sufficiently beyond the distal edge of the inner tubular member 20, the cutting elements 26, 26a begin to close (arrows 27) and the cutting edges 28, 28a sever the tissue sample from the body surface 18. The cutting member may be rotated slightly about its axis as it is extended forward to create a shearing action to facilitate cutting. As tissue enters the inner tubular member it pushes the previously-taken samples, samples 1–4, proximally in the space 25.

Figure 2C:
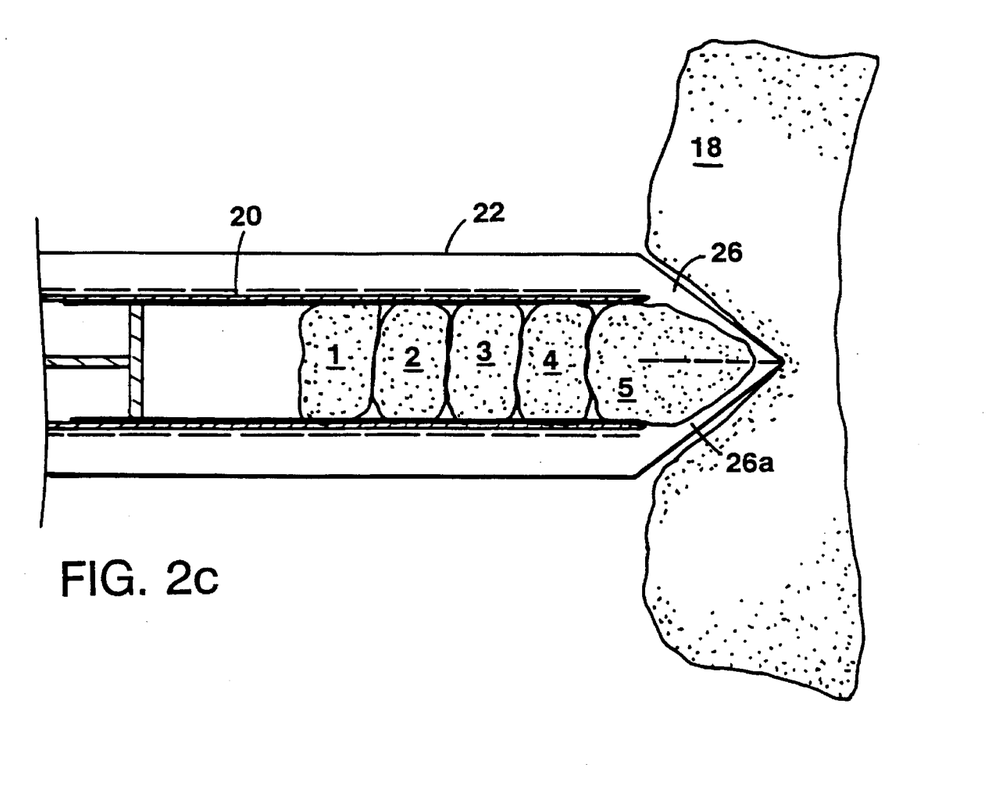

Referring particularly to FIG. 2c, after the cutting member 22 has been extended distally such that the cutting elements 26, 26a are completely closed, the new sample, sample 5, is cut completely free of the tissue surface 18.

Figure 2D:
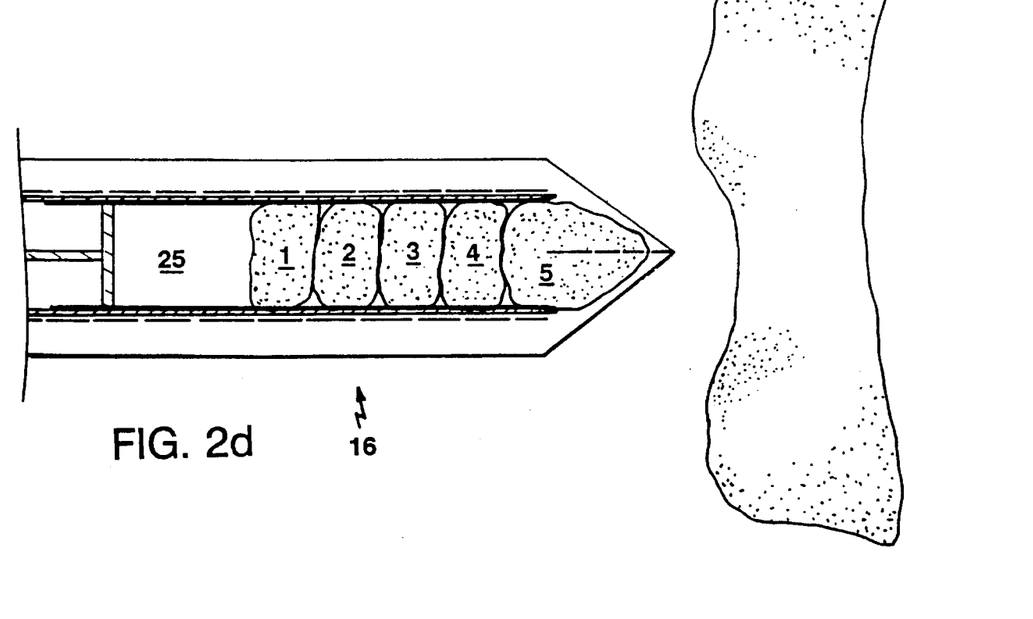

Referring particularly to FIG. 2d, the device 16 can be moved to a new location for taking an additional sample by repeating the steps above. Thus, multiple samples can be taken without removing the device from the body.

Figure 2E:
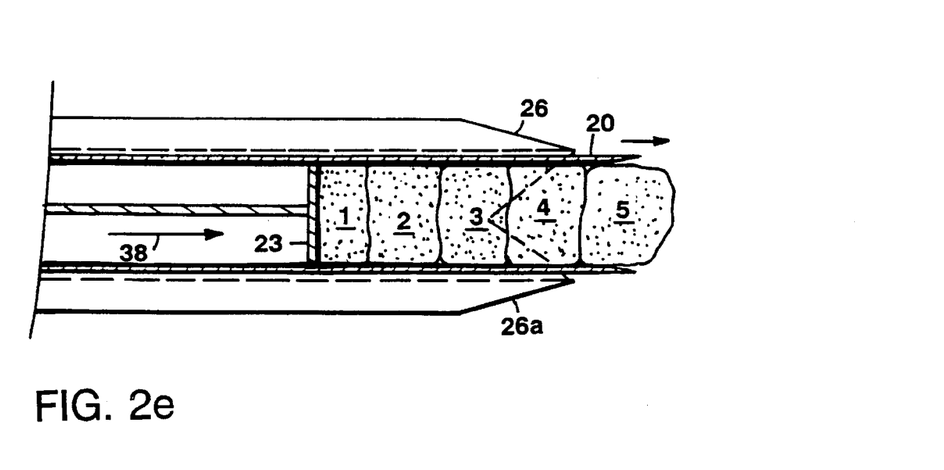

Referring to FIG. 2e, after a sufficient number of samples have been taken, and the device has been removed from the body, samples 1–5, stored in the space 25 in the order in which they were taken, can be recovered by again extending the inner tubular member 20 in the distal direction to force open the cutting elements 26, 26a. The stop member 23 is then extended distally (arrow 38) to push the samples sequentially from the end of the tubular member.

Figure 3:
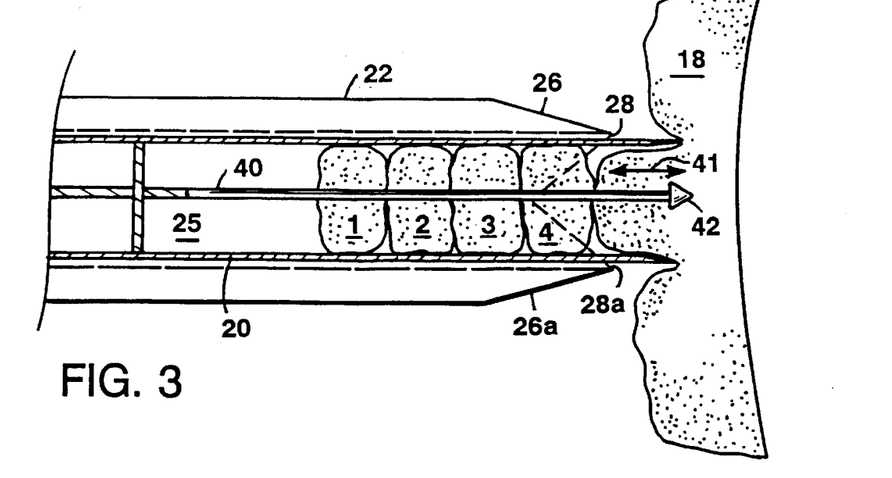
FIG. 3 illustrates the structure and use of another embodiment of the invention.

Referring to FIG. 3, another embodiment is shown. In this case, a retractor member 40 is provided. The retractor member is axially movable (arrow 41), is formed of an extended length, and has a barbed tip 42 for piercing and retaining samples during axial travel. In use, the inner tubular member 20 is extended to open cutting elements 26, 26a and to rest against the tissue surface 18. The distal end of the tubular member may include, but does not require, a sharp cutting edge. The retractor 40 is then extended distally into the surface 18, thus displacing previous samples 1–4 proximally along its body. The retractor 40 is then withdrawn proximally drawing a piece of tissue into the distal end of the tubular member 20, as shown in FIG. 3. The cutting member 22 can then be moved distally to close the cutting elements 26, 26a and sever the sample from the surface 18. Other retractors can be used, such as hooks, tongues, and helical screw elements as described, for example, in "Multiple Biopsy Sampling Device", by Bruce H. Diamond, Donald E. Robinson, Alyssa J. Dassa, and Charles Warich, U.S. Ser. No. 08/124, 272, filed Sep. 20, 1993, the entire contents of which is hereby incorporated by reference. Also incorporated by reference is "Multiple Biopsy Sampling Forceps" by Alyssa J. Dassa and Bruce H. Diamond, U.S. Ser. No. 08/128,653, filed Sep. 30, 1993.

The embodiment of FIG. 3 can also be used by providing the tubular member with a sharpened distal end and extending the tubular member 20 into the tissue, as described above with respect to FIGS. 2 et seq. The retractor is positioned so it pierces the tissue that passes through the distal opening. However, rather than pushing the cutting member 22 in the distal direction to close the jaws, the tubular member 20 and retractor 40 are withdrawn proximally together relative to the moveable cutting elements, which close to sever the sample. The cutting member may be rotated as the inner tubular member is drawn proximally, to cause a shearing action that enhances cutting.

Figure 4:
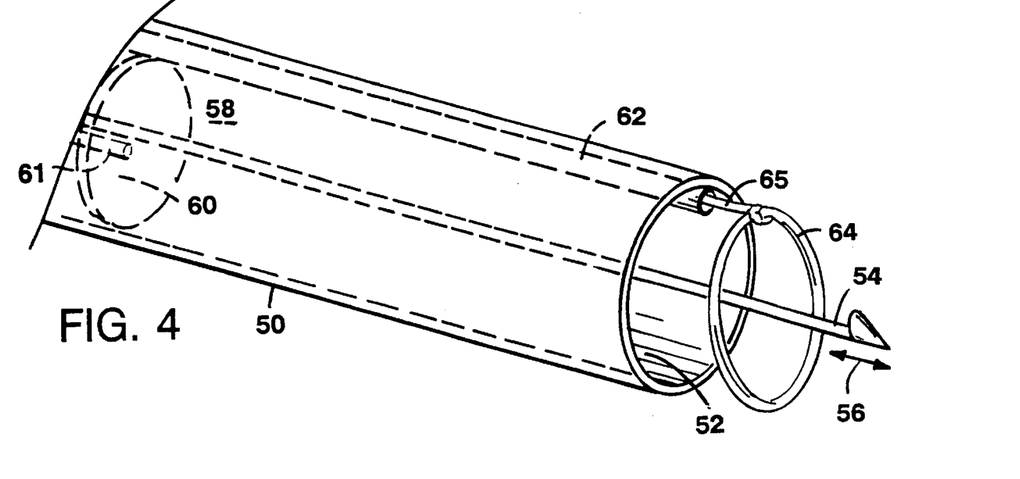
FIGS. 4–4e illustrate the structure and use of another embodiment of the invention.
Figure 4A:
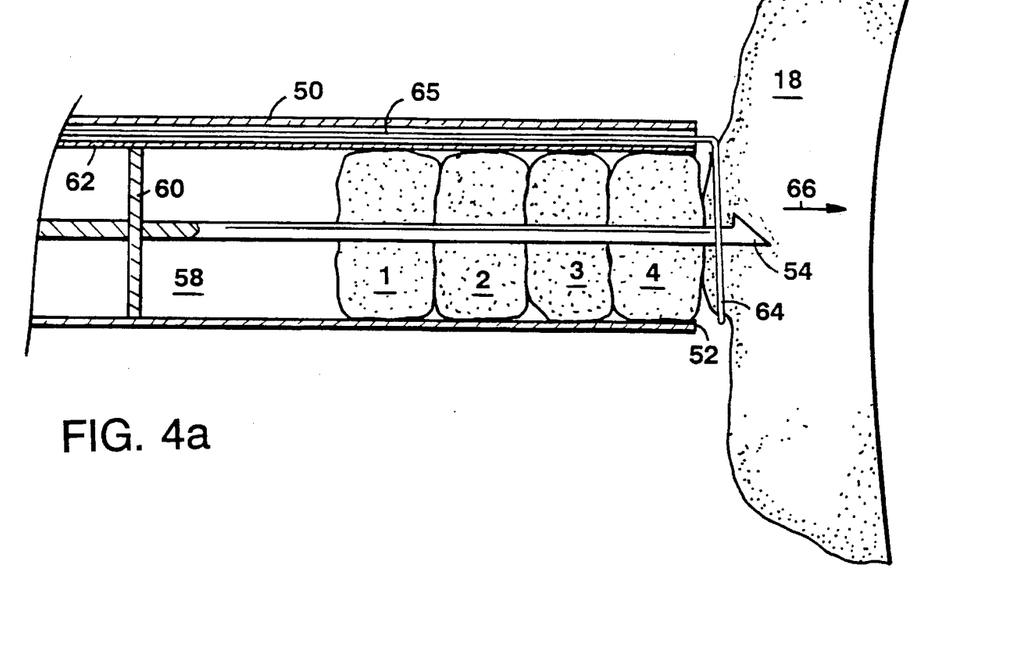
Figure 4B:
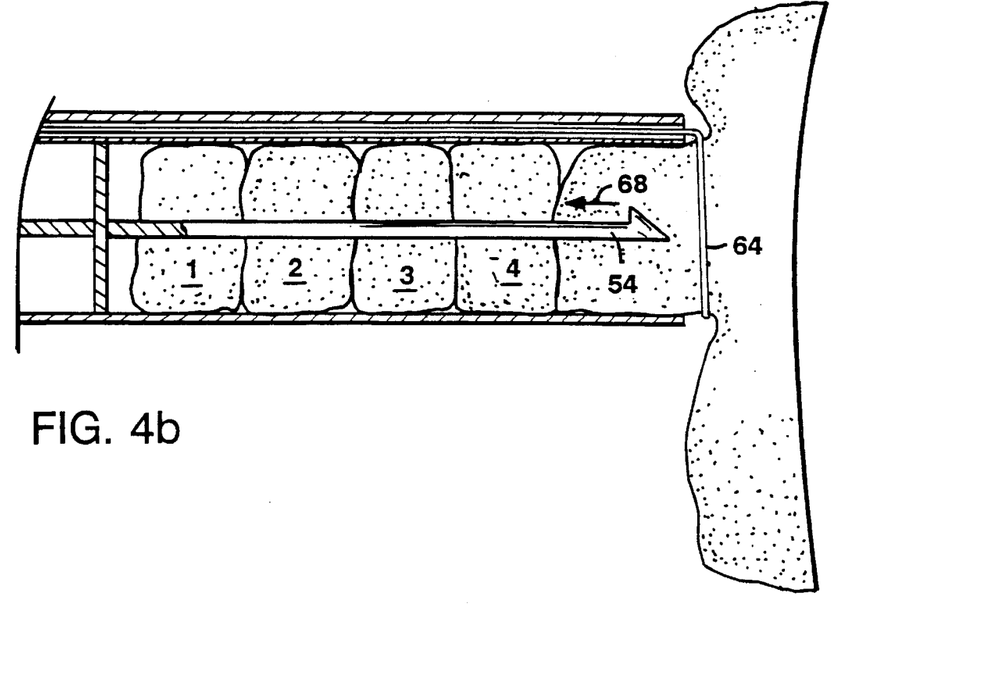
Figure 4C:
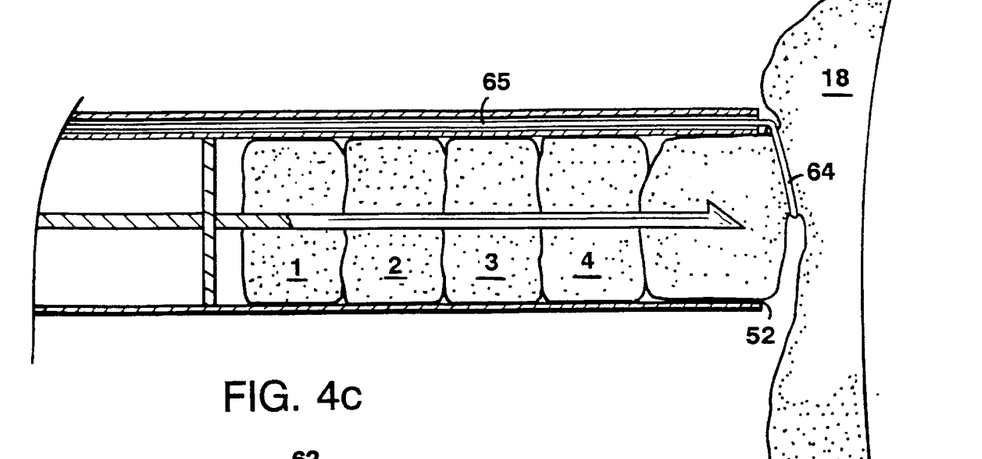
Figure 4D:
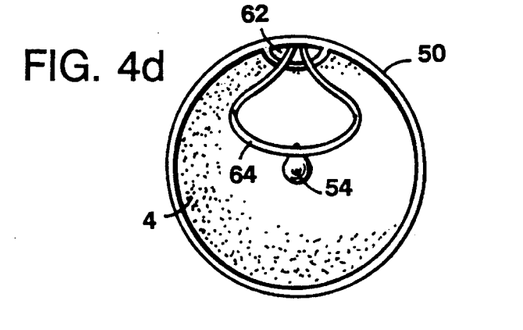
Figure 4E:
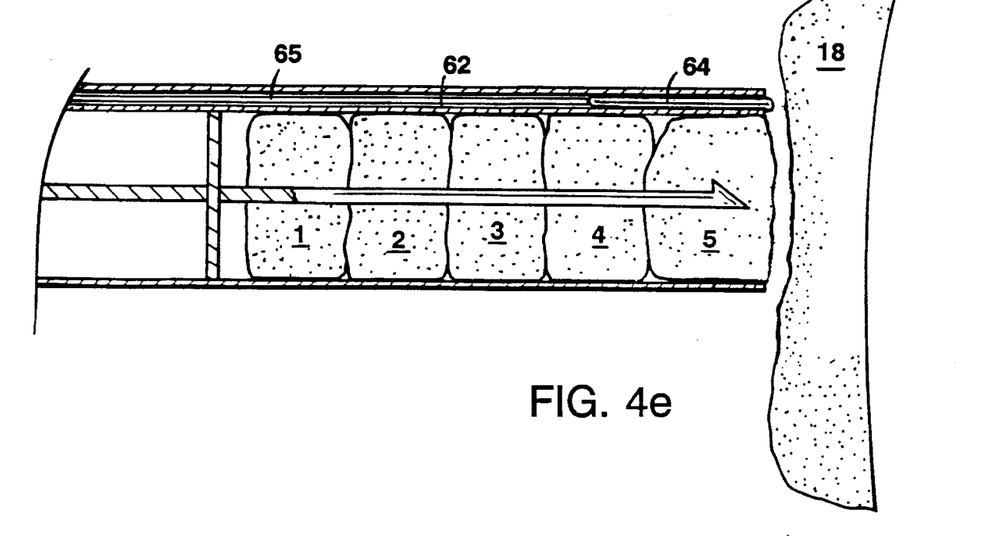

Referring to FIGS. 4–4e, another embodiment is shown. In this embodiment, a tubular member 50 defines at its distal end, a forward-facing distal opening 52 and includes within a retractor 54, preferably a spear-form element with a barb as shown, or another retractor type as discussed above. The retractor 54 is axially movable (arrow 56) and extends through a storage space 58 bounded on the proximal end by a sample stop 60. The axial motion of the retractor 54 and stop 60 are controlled separately; the retractor passes through an aperture in the stop and the stop is controlled by a separate member 61. (Alternatively, in other embodiments, the retractor may be attached to the stop so they move axially together.)

The embodiment also includes a wire-form cutting loop 64. The loop, shown extended in FIG. 4, is oriented with its center roughly along the axis of the device and sized to approximate or be larger than the outer diameter of the distal portion of tubular member 50. The loop 64 may be formed of a shape memory metal, e.g., nitinol or other elastic materials, such as cold-worked stainless steel, or a plastic, that can be preformed and trained so it is capable of being repeatedly withdrawn into a lumen 62, where the loop is in a compacted state, and then extended therefrom to open and orient the loop as shown. A control wire 65, for retracting and extending the loop, may be made integrally or attached to the loop. The lumen 62 may be constructed integrally with the tubular member 50.

Referring particularly to FIG. 4a (cross-sectional view), in use, the control wire 65 is extended distally so the cutting loop 64 is formed and positioned just distal of the open end 52 of the device 50, which is brought in proximity of the surface 18 where a sample is be taken. The retractor 54 is extended distally (arrow 66) so it pierces the tissue surface 18. As the retractor 54 is extended distally, previously taken samples, samples 1–4, are displaced proximally.

Referring particularly to FIG. 4b, the retractor 54 is then withdrawn proximally (arrow 68), bringing tissue into the distal end opening of the member 50 and through the cutting loop 64.

Referring particularly to FIGS. 4c, 4d (end on view, tissue not shown) and 4e, the tissue sample is severed from the surface 18 by withdrawing the control wire 65 proximally, which draws the loop 64 through tissue across the end opening 52 of the member 50. With the loop 64 substantially withdrawn in the lumen 62, the new sample, sample 5, is completely severed from the surface 18 (FIG. 4e). The process can be repeated by extending control wire 65, distally and hence forming the cutting loop 64, to cut the next sample, as shown in FIG. 4a.

Figure 5:
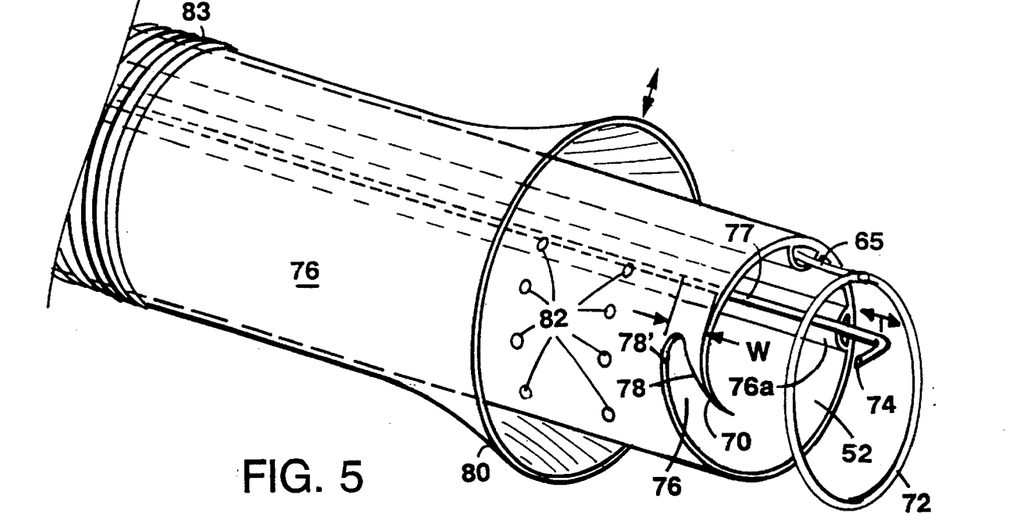
FIGS. 5–5e illustrate the structure and use of yet another embodiment of the invention.
Figure 5A:
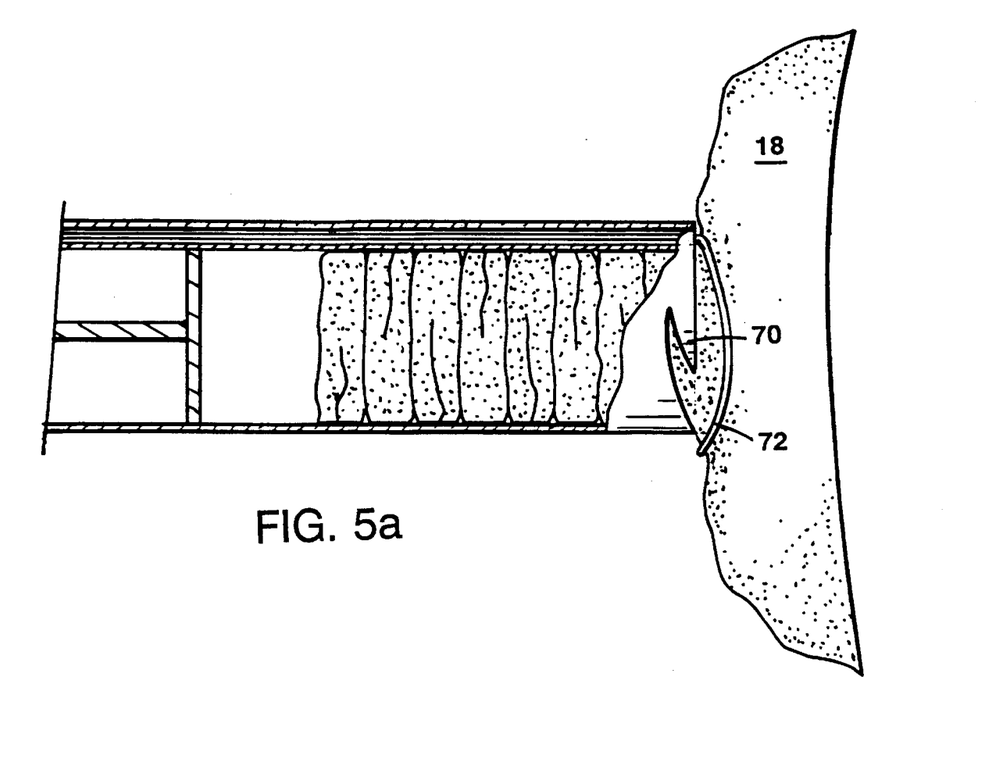
Figure 5B:
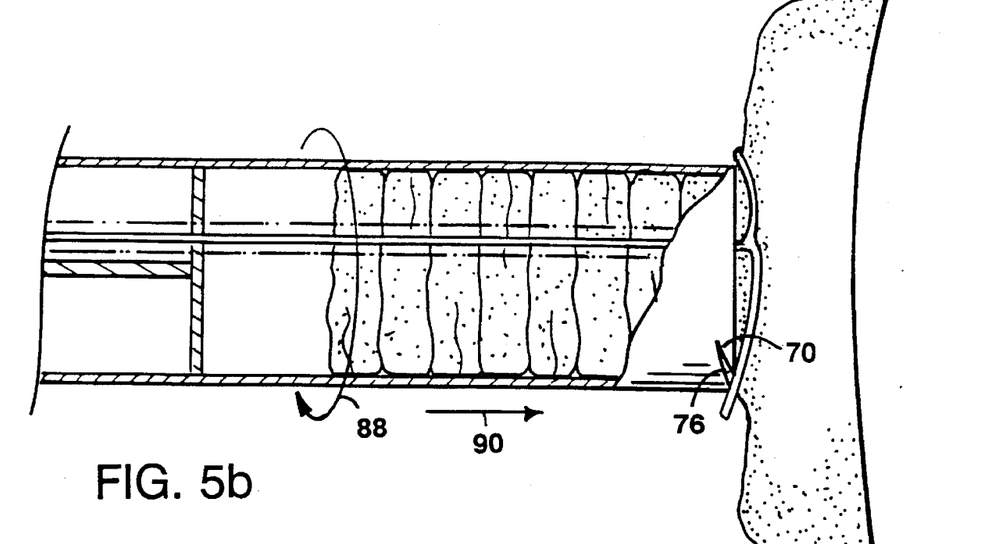
Figure 5C:
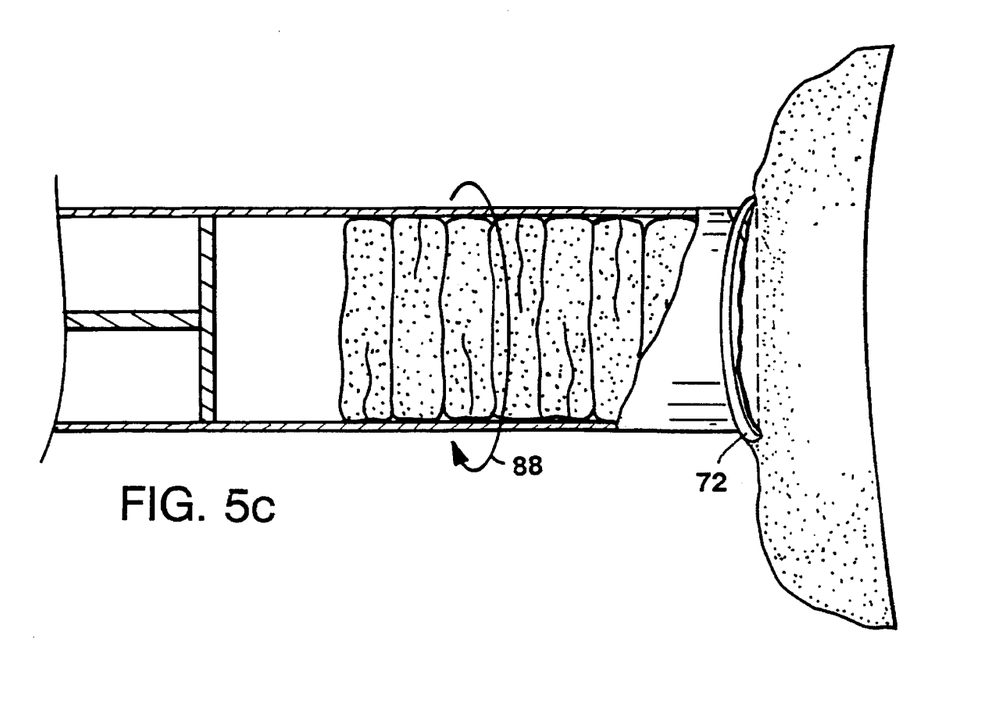
Figure 5D:
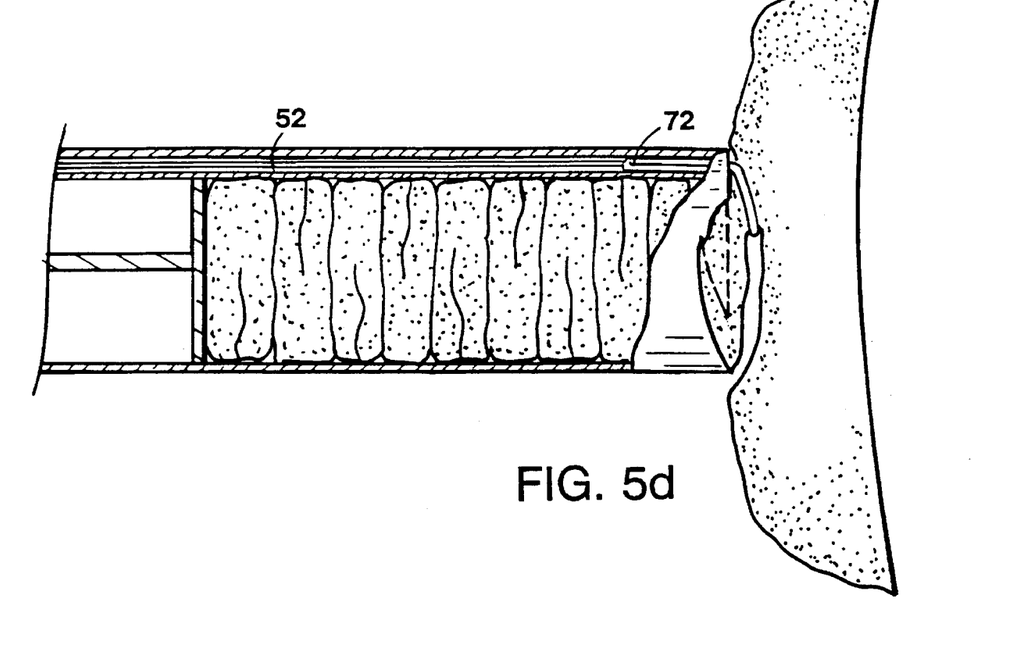
Figure 5E:
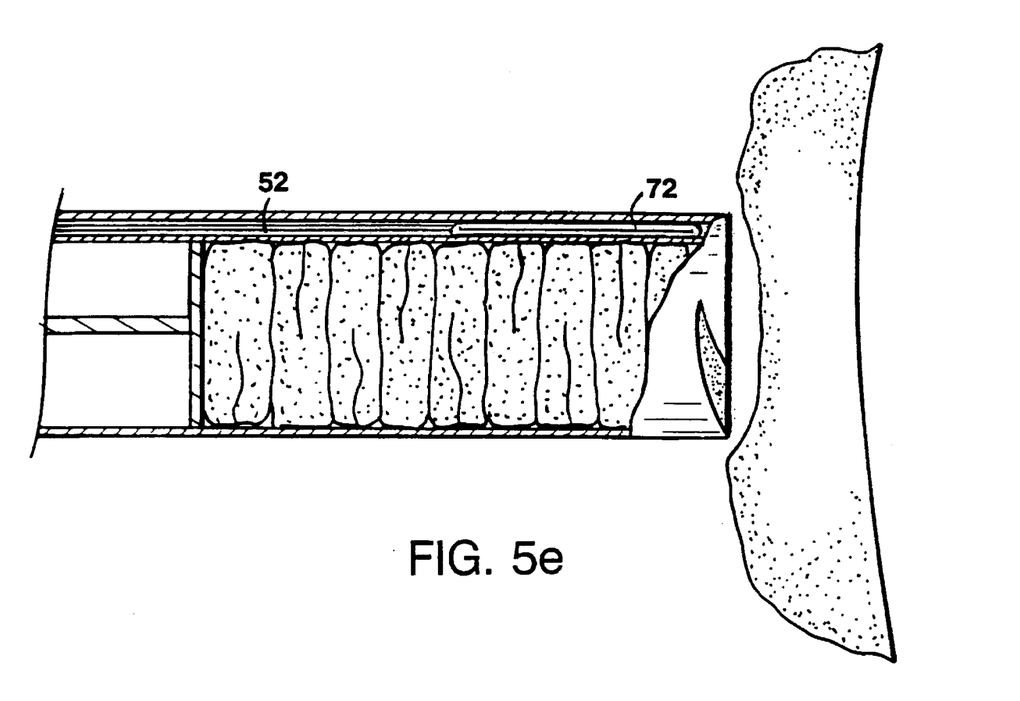

Referring to FIGS. 5–5e, another embodiment is shown. In this case, the device includes near the end opening 52, a cutting guide 70, formed in the wall of the tubular body adjacent the distal end. (The guide does not extend across the diameter of the end opening; rather, it is formed by cutting out a portion of the side wall of a tube.) The device further includes a cutting loop 72, having an open diameter larger than the diameter of the end 54 of the device.

In this embodiment, the depth of the sample cut can be carefully and conveniently controlled. The end 54 of the device is pressed against the tissue wall. (The end need not be sharpened to a tissue-cutting edge.) Tissue prolapses into the gap 76 proximal of the cutting guide 70. The gap is bordered by sharpened cutting edges 78, 78'. Thus, tissue cutting occurs only during rotation of the device. The depth of tissue cut during rotation is controlled by the width of the cutting guide W from the end 54 of the device to the lower-most proximal portion of the cutting edge 78. Thus, for a single rotation, a helical, circumferential cut through tissue is made to a depth no greater than the width W.

The cutting loop 72, of an enlarged diameter, slides distally over the body of the device as the distal end enters the tissue. The loop 72 can be retracted to sever the sample of controlled depth from the body surface. An axially movable retracting arm 74, passing through a slotted lumen 76a, may also be provided to pull samples into the body of the device for storage. The lumen slot 77 allows the radially extending arm to be withdrawn proximally. An optional stop member 80, in this case a conical member that widens to greater diameter in the distal direction, can be positioned on the device to assure that coring beyond a predetermined depth does not occur. The stop member can be an umbrella-type assembly that changes the axial location of the end of the stop by opening and closing radially, as shown. Other stop mechanisms, such as an inflatable balloon or a spring-form wire may also be used. Apertures 82 are placed in the body of the device so that fluids (e.g. ambient body fluids)

can easily pass to contact previously taken samples while they are being stored to keep them from drying out, which can damage cell structure and make pathological examination more difficult. Saline solution or the like may also be passed from proximal portions e.g. through the main lumen, into contact with samples. The saline may flow out of the apertures 82.

The body of the device is preferably formed of a highly torqueable plastic tube, but for the distal end including the cutting tang 70, which is preferably formed of metal. The proximal portions of the device include a wire coil body 83 that can be passed through torturous passageways, e.g., an endoscope channel. The shape of the guide can be varied to affect various depths and cutting profile. Typically, the most distal end of the guide terminates in a sharp point, as shown, to help start the cutting when rotation begins. The control wire and/or the cutting loop may be made of braided wires. The cutting loop may be shaped along its inner edge to form a sharp cutting surface. The cutting loop may also be heated e.g., by electric current. The end of the tubular member may flare outward, distally to facilitate drawing tissue into the end.

Referring particularly to FIG. 5a, in use, the enlarged cutting loop 72 is extended and the distal end of the device, including front-facing surface of the cutting guide 70, is pressed against the surface 18 of tissue from which a sample is be taken. Tissue prolapses into the gap 76 of the cutting guide. (This embodiment does not include retractor 74 or stop 80. The mechanical simplicity of this embodiment is an advantage, since, it can be delivered through tighter lumen tracts to hard-to-reach sampling sites.)

Referring particularly to FIG. 5b, the body of the device is pressed against the tissue and rotated about its axis (arrow 88), causing tissue in the gap 76 to be cut by the sharpened edges 78, 78'.

Referring particularly to FIG. 5c, as the distal end of the device enters the tissue due to the rotating cutting motion, the cutting loop 72 is pushed proximally, over the outside of the body.

Referring particularly to FIG. 5d, when the device has entered the tissue to a desired depth, for example, a single rotation of the device cutting to a depth equal to the width of the guide, a sample can be severed from the tissue surface 18 by withdrawing the cutting loop 72 into the lumen 52. The cutting loop, drawn back into the lumen 62 over the body, cuts the tissue across the opening of the distal end of the device.

Referring particularly to FIG. 5e, with the cutting loop 72 drawn substantially completely into the lumen 52, a thickness-controlled sample is severed from the tissue surface 18. The procedure above can be repeated to take an additional sample if desired.

Figure 6:
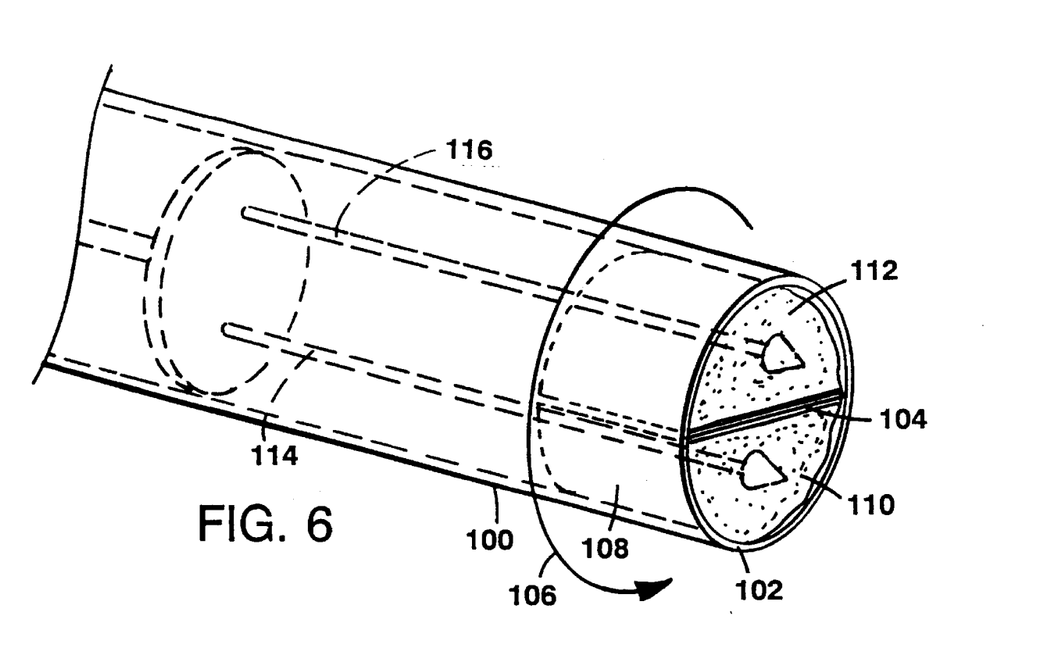
FIG. 6 illustrates the structure and use of another embodiment of the invention.

Referring to FIG. 6, another embodiment is shown. In this case, the device includes a tubular member 100, having an open tubular distal end 102. The distal end 102 is sharpened so the device may be urged into tissue to a desired depth, by extending the device distally axially. A cutting wire 104 is provided across the circumference of the device. To sever a tissue sample, the body of the device is rotated about its axis (arrow 106). For each sample taken, the device produces two sample halves. For example, sample halves 110, 112 of sample 108, since the tissue has been bisected by the cutting wire 104 when the device was urged distally into the tissue surface. The device may further be provided with retractor members 114, 116, which may be in the form of a spear-form element or other retractors as described above.

Figure 7:
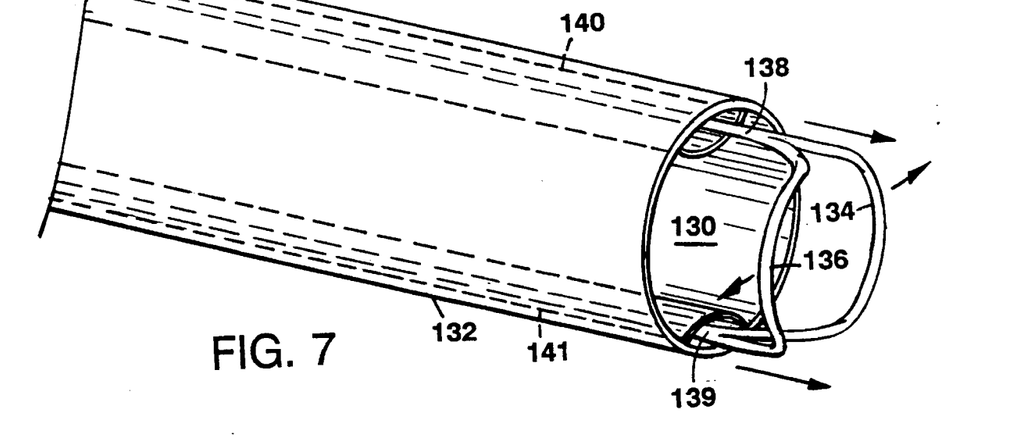
FIGS. 7–7c illustrate the structure and use of another embodiment of the invention.
Figure 7A:
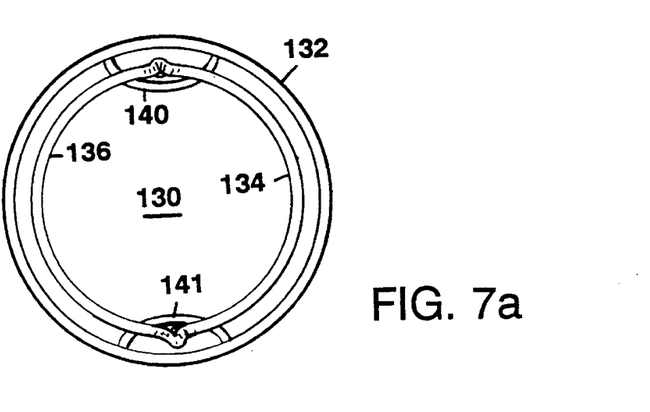
Figure 7B:
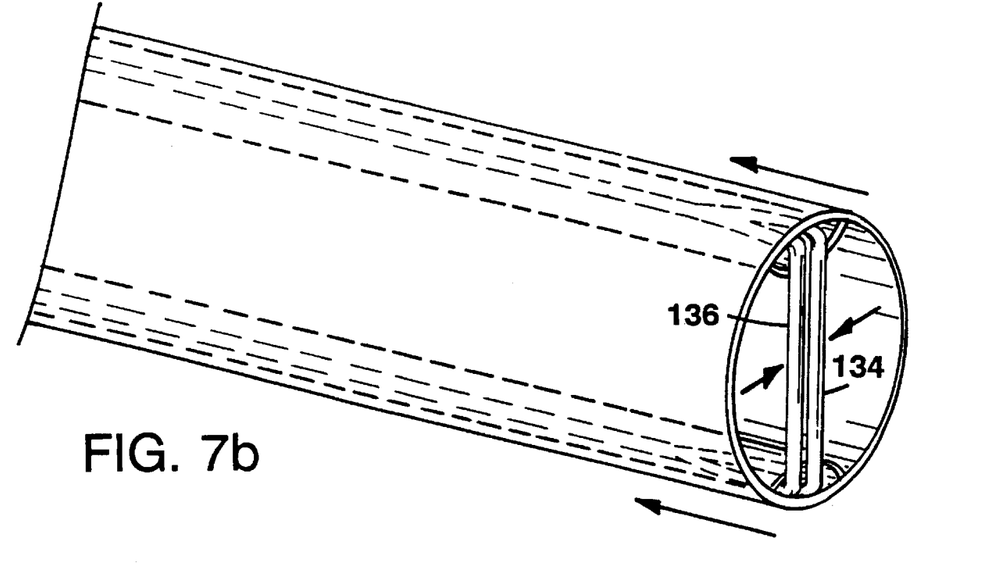
Figure 7C:
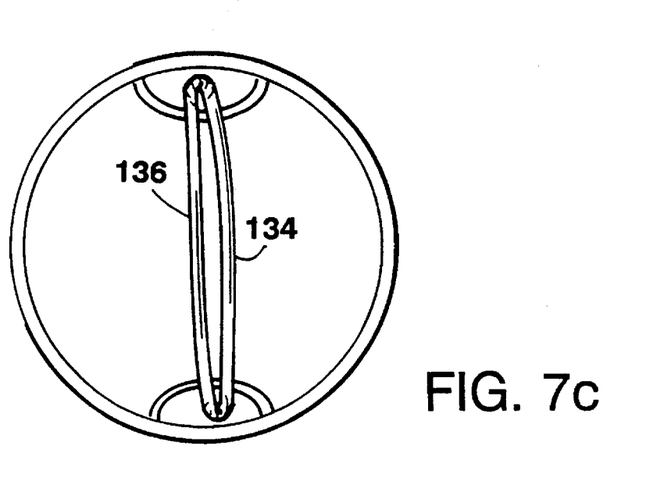

Referring to FIGS. 7–7c, another embodiment for severing tissue is shown. In this case, an arrangement for severing tissue across the distal end 130 of a tube 132 includes a pair of wire cutting elements 134, 136, that join at respective ends to control wires 138, 139, that are axially moveable in lumens 140, 141. In the configuration shown in FIGS. 7 and 7a (end-on view), the control wires are extended, which bows the wire cutting elements 134, 136 outward, causing them to conform to the outer end of the tubular member so that tissue can extend beyond the wires and enter the distal end of the tube. In the configuration of FIGS. 7b and 7c, the control wires are drawn proximally, causing the cutting elements 134, 136 to close across the end opening of the tube, cutting tissue so that a sample can be severed from a tissue surface. In other embodiments, a single control wire is used; the other ends of the cutting elements are attached to the end of the tube.

The features discussed above with respect to the various embodiments, e.g. arrangements for receiving tissue through the opening of the devices and arrangements for severing tissue from a surface, can be combined in further embodiments.

Still further embodiments are within the following claims.

What is claimed is:

1. A device for collecting from a tissue surface, a sample of tissue, including tissue specimens, polyps, or the like, the device being flexible and elongated for introduction to a biopsy site deep within the body, comprising:

a device body having a distal end defining a forward-facing tissue receiving opening of substantially predetermined width through which a core portion of tissue may pass when said opening is near said tissue surface, a separate severing element actuatable across the width of said tissue receiving opening when tissue from said surface extends through said opening for severing said core portion of tissue from said tissue surface, wherein said severing element comprises a set of moveable, jaw-like cutting members actuatable to be opened and closed for severing tissue from said surface to take said sample, said cutting members being coaxially disposed over said device body and axially positionable with respect to said tissue receiving opening such that said device is positionable between a first configuration in which the cutting members are proximal of said opening for receiving tissue through said opening and a second configuration in which the cutting members are distal of said opening where said cutting members can be closed to sever tissue and take said sample, a storage space within said device body at a location proximal of and adjacent said opening for storage of multiple successively taken samples by repeatedly passing tissue through said opening and actuating said severing element and a sample stop positioned within said storage space and being axially positionable with respect to said tissue receiving opening such that said stop is positionable between a first position in which said stop defines a proximal end of said storage space and a second position distally located with respect to said first position for retrieving samples from said storage space by pushing said samples distally through said opening.

2. The device of claim 1 wherein said cutting members are biased closed, said cutting members being openable by disposing said device in the first configuration, where said cutting members bear on outer surfaces of the body which oppose said bias, and said cutting members are closed by disposing said device in the second configuration where said jaws are free from said body and close in response to said bias.

3. A method for collecting from a tissue surface, a sample of tissue, including specimens, polyps, or the like, comprising:

providing a sampling device being flexible and elongated constructed for introduction to a biopsy site within the body, including:

a device body having a distal end defining a forward-facing tissue receiving opening of substantially predetermined width through which a core portion of tissue may pass when said opening is near said tissue surface, a separate severing element actuatable across the width of said tissue receiving opening when tissue from said surface extends through said opening for severing said core portion of tissue from said tissue surface, wherein said severing element comprises a set of moveable, jaw-like cutting members actuatable to be opened and closed for severing tissue from said surface to take said sample, said cutting members being coaxially disposed over said device body and axially positionable with respect to said tissue receiving opening such that said device is positionable between a first configuration in which the cutting members are proximal of said opening for receiving tissue through said opening and a second configuration in which the cutting members are distal of said opening where said cutting members can be closed to sever tissue and take said sample, a storage space within the device body proximal of and adjacent said opening for storage of multiple successively taken samples by repeatedly passing tissue through said opening and actuating said severing element, and a sample stop positioned within said storage space and being axially positionable with respect to said tissue receiving opening such that said stop is positionable between a first position in which said stop defines a proximal end of said storage space and a second position distally located with respect to said first position for retrieving samples from said storage space by pushing said samples distally through said opening, delivering said device by threading said device through the body to a desired tissue surface deep within the body, positioning said device near said tissue surface, receiving said core portion of tissue through said tissue-receiving opening, actuating said severing element to sever said core portion of tissue from said surface, repeating said steps of positioning and actuating to take multiple samples without removing said device from the body, removing said device from the body, positioning said cutter in said first configuration such that said cutting members are proximal of said tissue-receiving opening, and retrieving said samples by actuating said stop to said second position to push said samples distally through said tissue opening.

4. The method of claim 3, comprising:

delivering said device through on endoscope.

5. In an instrument for obtaining tissue samples, the instrument sized and constructed to pass through a working channel of an endoscope to take samples, including tissue specimens, polyps or the like, from a tissue surface under endoscopic guidance and having a proximal and distal end, said instrument constructed to sever and remove a tissue sample from the body, the improvement wherein said instrument is constructed to take multiple biopsy samples without being withdrawn from the endoscope, said instrument including:

a device body defining at its distal end a forward-facing tissue receiving opening of substantially predetermined width through which a core portion of tissue may pass when said opening is near said tissue surface, a separate severing element actuatable across the width of said tissue receiving opening when tissue from said surface extends through said opening for severing said core portion of tissue from said tissue surface, wherein said severing element comprises a set of moveable, jaw-like cutting members actuatable to be opened and closed for severing tissue from said surface to take said sample, said cutting members being coaxially disposed over said device body and axially positionable with respect to said tissue receiving opening such that said device is positionable between a first configuration in which the cutting members are proximal of said opening for receiving tissue through said opening and a second configuration in which the cutting members are distal of said opening where said cutting members can be closed to sever tissue and take said sample, a storage space within said device body proximal of and adjacent said opening for storage of multiple successively taken samples by repeatedly passing tissue through said opening and actuating said severing element to accumulate a series of samples without withdrawing the instrument from the endoscope and a sample stop positioned within said storage space and being axially positionable with respect to said tissue receiving opening such that said stop is positionable between a first position in which said stop defines a proximal end of said storage space and a second position distally located with respect to said first position for retrieving samples from said storage space by pushing said samples distally through said opening.

* * * * *